(12) United States Patent
Kaplan et al.

(10) Patent No.: US 10,517,609 B1
(45) Date of Patent: Dec. 31, 2019

(54) SUTURE DRILL APPARATUS AND METHOD

(71) Applicants: Andrew S. Kaplan, Burlington, VT (US); Daniel S. Pflaster, Charlotte, VT (US)

(72) Inventors: Andrew S. Kaplan, Burlington, VT (US); Daniel S. Pflaster, Charlotte, VT (US)

( * ) Notice: Subject to any disclaimer, the term of this patent is extended or adjusted under 35 U.S.C. 154(b) by 672 days.

(21) Appl. No.: 14/850,692

(22) Filed: Sep. 10, 2015

Related U.S. Application Data

(60) Provisional application No. 62/048,298, filed on Sep. 10, 2014.

(51) Int. Cl.
*A61B 17/16* (2006.01)
*A61B 17/06* (2006.01)

(52) U.S. Cl.
CPC .... *A61B 17/1615* (2013.01); *A61B 17/06004* (2013.01); *A61B 17/06119* (2013.01); *A61B 17/162* (2013.01); *A61B 17/1631* (2013.01); *A61B 2017/06052* (2013.01)

(58) Field of Classification Search
CPC ..... A61B 17/04; A61B 17/16; A61B 17/1615; A61B 17/1617; A61B 17/162; A61B 17/17; A61B 17/06; A61B 17/1631; A61B 17/1637; A61B 17/1655; A61B 17/1697; A61B 17/06061; A61B 17/06114; A61B 17/06119; A61B 17/06123; A61B 17/06128; A61B 17/06133; A61B 17/06138; A61B 17/1622; A61B 17/1633; A61F 2/08

USPC .......................................................... 606/148
See application file for complete search history.

(56) References Cited

U.S. PATENT DOCUMENTS

| | | | | |
|---|---|---|---|---|
| 919,152 | A * | 4/1909 | Gause | A61B 17/04 606/146 |
| 3,654,911 | A * | 4/1972 | Loge | A61B 17/1697 606/180 |
| 4,510,934 | A * | 4/1985 | Batra | A61B 17/06 428/377 |
| 5,055,105 | A * | 10/1991 | Hamlin | A61B 17/1615 408/224 |
| 5,611,801 | A * | 3/1997 | Songer | A61B 17/82 606/103 |
| 5,857,995 | A * | 1/1999 | Thomas | A61B 17/1615 604/22 |
| 6,315,784 | B1 * | 11/2001 | Djurovic | A61B 17/06109 606/146 |
| 6,620,185 | B1 * | 9/2003 | Harvie | A61B 17/0401 606/215 |
| 7,645,293 | B2 * | 1/2010 | Martinek | A61B 17/0401 606/232 |
| 2003/0158562 | A1 * | 8/2003 | Feigl | A61B 17/0482 606/148 |

* cited by examiner

*Primary Examiner* — Kathleen S Holwerda
*Assistant Examiner* — Kankindi Rwego
(74) *Attorney, Agent, or Firm* — J. Nevin Shaffer, Jr.

(57) ABSTRACT

A suture drill apparatus and method includes a drill shaft with a first end and a second end where the drill shaft is conformed to connect with a drill and where the drill shaft includes a first diameter and a second diameter and the first diameter is larger than the second diameter and a suture is connected with the drill shaft.

20 Claims, 4 Drawing Sheets

US 10,517,609 B1

SUTURE DRILL APPARATUS AND METHOD

CROSS REFERENCE TO RELATED APPLICATION

This application claims the benefit of previously filed U.S. provisional patent application No. 62/048,298 filed Sep. 10, 2014 for a "Suture Drill Apparatus and Method". The Applicants hereby claim the benefit of this provisional application under 35 U.S.C. § 119. The entire content of this provisional application is incorporated herein by this reference.

FIELD OF THE INVENTION

The invention relates generally to devices for repairing bone and soft tissue (e.g. muscle, tendon, ligament). More specifically, the invention relates to devices used to drill through bone and soft tissue and passing sutures through the drilled holes. In particular, according to one embodiment, a suture drill apparatus consists of a drill shaft with a first end and a second end where the drill shaft is conformed to connect with a drill and where the drill shaft includes a first diameter and a second diameter and the first diameter is larger than the second diameter and a suture is connected with the drill shaft.

BACKGROUND OF THE INVENTION

A problem exists with regard to the use of sutures. Currently, a suture is attached to bone by either a suture anchor or transosseos bone tunnels. Suture anchors can be problematic due to their cost, the requirement of multiple steps for deployment and because they are left in place permanently in the bone, often adversely affecting future imaging (especially with MRI scanning) as well as having the potential to create problems in future surgeries in the same area where metal or plastic implants remain years after an initial procedure. They can create problems by being in the way during a subsequent or revision approach to that joint.

Bone tunnels can also be problematic, as they require two steps: first a drilling procedure followed by a suture passing procedure. Additionally, the surgeon can lose the location of the bone tunnel between the steps of drilling and suture passing, lengthening the procedure time and possibly necessitating another tunnel to be drilled (creating essentially a third step to the procedure).

Further, the drill hole must be of sufficient diameter to allow passing of the suture, which according to the art is doubled to pass through the bone using a suture passer, creating a tunnel that is at least two times the required diameter to contain the suture. The larger tunnel weakens the bone and can lead to catastrophic boney fractures. Oversized bone tunnels have also been observed to get bigger over time, possibly due to synovial fluid extravisation out of a joint through the bone tunnels, further weakening the bone.

Additionally, presently when trying to simply pass suture through a straight drill hole made in bone, many sutures are swedged onto needles, but most needles are curved needles, making a tunnel/needle shape mismatch. Problems can be created by this including breaking through the tunnel, misdirection through the tunnel, or as surgeon attempts to straighten the curved needle to match the tunnel trajectory sometimes needles break and sometimes needle breakage occurs while passing in the bone tunnel, causing inadvertent implanting of needle parts or a frustrating and time consuming struggle to remove a broken needle.

Thus, there is a need in the art for an apparatus and method for using sutures that eliminates the problems of prior art processes and provides an easy to use device that saves time and money.

It, therefore, is an object of the present invention to provide a suture drill device that eliminates multiple prior art steps for the administration of sutures in a medical procedure that is time and cost efficient, accurate, repeatable and safe.

SUMMARY OF THE INVENTION

Accordingly, in particular, according to one embodiment, a suture drill apparatus of the present invention consists of a drill shaft with a first end and a second end where the drill shaft is conformed to connect with a drill and where the drill shaft includes a first diameter and a second diameter and the first diameter is larger than the second diameter and a suture is connected with the drill shaft.

All terms used herein are given their common meaning so that "drill shaft" describes a length of material. The drill shaft may include a circular diameter, round or otherwise, yet the diameter is less than its length. A metal shaft, wire or the like is included in the meaning of drill shaft. Whatever material it is made of, the drill shaft of the present invention must be strong enough such that, when attached to a drill, the drill shaft penetrates the material to which it is applied, such as, for example only, flesh and bone.

Importantly, the drill shaft of the present invention includes a "first diameter" and a "second diameter" where the first diameter is larger than the second. By this is described a shaft, such as a metal shaft of generally uniform diameter along its length yet one which has at least some section with a larger first diameter as described more fully hereafter.

"Drill" describes a device for manipulating a drill shaft to create a hole, as is known. Thus, the term "drill" includes manual and motorized drills, battery powered cordless and corded drills. Importantly, the drill of the present invention is a cannulated drill, that is a drill with a center hole through which the drill shaft of the present invention passes and is retained while drilling, as shown and described more fully hereafter.

Likewise, the term "suture" is given its common meaning as used by those of ordinary skill in the art and includes sutures made of any material such as thread, woven or otherwise, wire and tape, for example only and not by way of limitation.

According to one aspect, the invention further includes a suture cassette where the suture is enclosed within the suture cassette. In another aspect, the suture cassette includes an attachment device such that the suture cassette is removably connectable with the drill shaft and such that the suture cassette rotates with the drill shaft when connected with the drill shaft.

In one aspect, the first end of the drill shaft includes a drill head where the drill head forms the larger first diameter. In another aspect, the first end of the drill shaft includes a larger first diameter section and the second end includes a smaller second diameter section. In one aspect, the larger first diameter starts at the first end of the drill shaft and tapers along the drill shaft from the first end to the second end.

In another aspect, the apparatus further includes more than one suture connected with the drill shaft. In one aspect, the suture includes a first end and a second end and the first end of the suture is connected with the drill shaft and the second end of the suture includes a loop. In a further aspect, the second end of the suture is connected with a needle.

According to another embodiment, a suture drill apparatus consists of a drill shaft with a first end and a second end where the drill shaft is conformed to connect with a drill and where the drill shaft includes a first diameter and a second diameter and the first diameter is larger than the second diameter. A suture is connected with the drill shaft such that the suture extends from the second end of the drill shaft. A suture cassette is provided where the suture is enclosed within the suture cassette, where the suture cassette includes an attachment device such that the suture cassette is removably connectable with the drill shaft and such that the suture cassette rotates with the drill shaft when connected with the drill shaft.

In one aspect, the drill shaft is selected from a group consisting of: a drill shaft with an acorn tip; a drill shaft with a stepped diameter and a drill shaft that is tapered from the first end to the second end.

In another aspect, the suture is selected from a group of sutures consisting of: thread, flexible wire and implantable tape.

In one aspect, the suture cassette includes a spool and the suture is wound upon the spool within the suture cassette.

In another aspect, the drill shaft includes at least one channel in the drill shaft, the at least one channel starting at the second end of the drill shaft and extending along the length of the drill shaft with an opening in the drill shaft at the first end of the drill shaft, the at least one channel conformed to receive the suture.

One aspect further includes more than one suture connected with the drill shaft.

In another aspect, the suture includes a first end and a second end and the first end of the suture is connected with the drill shaft and the second end of the suture includes a loop. In a further aspect, the second end of the suture is connected with a needle.

According to another embodiment, a suture drill method consists of the steps of:
  a. providing a drill shaft with a first end and a second end where the drill shaft is conformed to connect with a drill and where the drill shaft includes a first diameter and a second diameter and the first diameter is larger than the second diameter; and a suture connected with the drill shaft such that the suture extends from the second end of the drill shaft;
  b. drilling a hole with the drill shaft;
  c. removing the drill from the drill shaft; and
  d. pulling the drill shaft and the suture through the hole.

In another aspect, the drill shaft is selected from a group consisting of: a drill shaft with an acorn tip; a drill shaft with a stepped diameter and a drill shaft that is tapered from the first end to the second end.

One aspect further includes a suture cassette where the suture cassette includes an attachment device such that the suture cassette is removably connectable with the drill shaft and such that the suture cassette rotates with the drill shaft when connected with the drill shaft and where the suture cassette is removed from the drill shaft after drilling the hole allowing the suture to be pulled out of the suture cassette while the suture remains attached to the drill shaft.

DESCRIPTION OF THE DRAWINGS

Other objects, features and advantages of the present invention will become more fully apparent from the following detailed description of the preferred embodiment, the appended claims and the accompanying drawings in which:

FIGS. 1 A-C are side views of the suture drill apparatus of the present invention including a suture cassette where

FIGS. 2 A-D are side views where.

FIGS. 3 A-D are side views of the invention of FIG. 1 illustrating various embodiments of sutures of the present invention where

FIGS. 4 A-C illustrate the drill shaft of the invention of FIG. 1 including a channel in the drill shaft where FIG. 5D shows the drill shaft and suture pulled through the hole.

DETAILED DESCRIPTION OF THE INVENTION

Figure 1A:
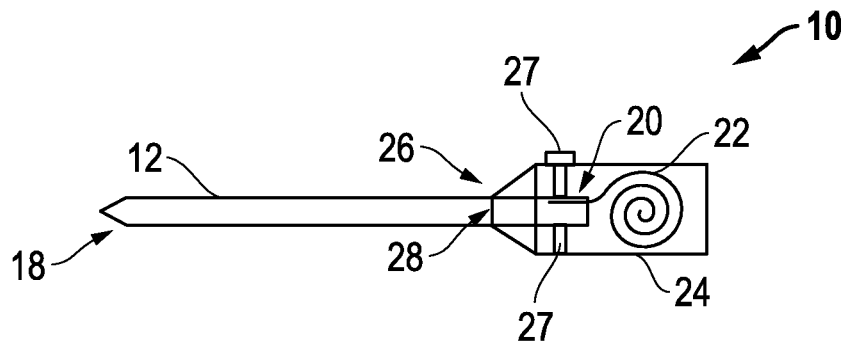
FIG. 1A shows the suture wound upon itself within the suture cassette.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

A preferred embodiment of the present invention is illustrated by way of example in FIGS. 1-5. With specific reference to FIGS. 1 and 2, suture drill apparatus 10 includes drill shaft 12. Again, drill shaft 12 is made of any sturdy material, such as, for example only, metal, ceramic, plastic and the like, capable of drilling a hole in a selected material. FIGS. 1A-C show drill shaft 12 of a uniform diameter only for the purpose of initial understanding of the various elements of the suture drill apparatus 10. That is, drill shaft 12 according to the preferred embodiment includes a first diameter 14 and a second diameter 16 where the first diameter 14 is larger than the second diameter 16 as shown and described more fully in FIGS. 2B-C, for example.

Drill shaft 12 has a first end 18 and a second end 20. Suture 22 is attached to drill shaft 12. Suture 22 may be attached to drill shaft 12 by any useful means such as tied, taped, press fit or swedged or secured by screws to drill shaft 12 all as may be deemed most useful for the circumstance. Preferably, as shown, suture 22 is connected with drill shaft 12 at the second end of drill shaft 12 however suture 22 may be connected with drill shaft 12 in other manners as, for example only, described with reference to FIGS. 4A-C.

According to one embodiment, the invention includes suture cassette 24. Suture cassette 24 is a container for holding suture 22. Suture cassette 24 is, preferably but not by limitation, attached to the second end 20 of drill shaft 12 by attachment device 26. Attachment device 26 preferably is a press fit connection. That is, an opening 28 in suture cassette 24 is just smaller than the diameter of drill shaft 12 at its second end 20. Opening 28 is forced to expand slightly by the drill shaft 12 such that the second end 20 is gripped tightly by opening 28. Certainly, any type of attachment device 26 may be used so long as once attached, suture cassette 24 rotates with drill shaft 12 when it is rotated. Thus, FIG. 1 A shows suture cassette 24 also connected to drill shaft 12 by means of pin 27. Pin 27 passes though suture cassette 24 and drill shaft 12 and thereby holds suture cassette 24 removably connected with drill shaft 12. Likewise, attachment device 26 may be in the form of a spring 29 connected with suture cassette 24 where spring 29 fits into notch 31 on drill shaft 12 and thereby holds suture cassette 24 removably in place on drill shaft 24.

Figure 1B:
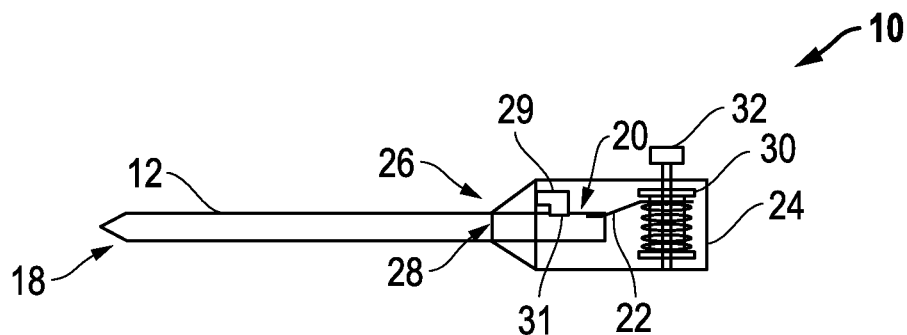
FIG. 1B shows the suture wound around a spool within the suture cassette.
Figure 1C:
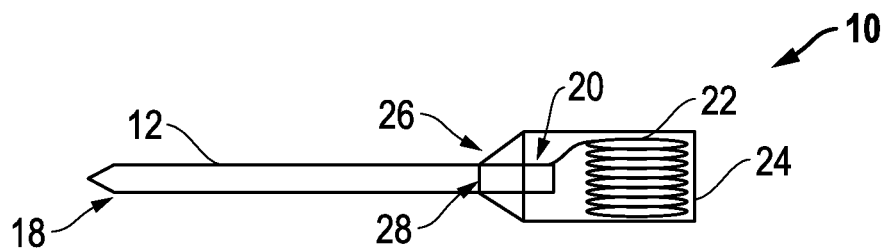
FIG. 1C shows the suture overlappingly laid upon itself within the suture cassette.

Importantly, suture cassette 24 holds suture 22 securely in place while drill shaft 12 is rotating to drill a hole, for example, thus preventing suture 22 from becoming snarled or entangled. FIG. 1A shows suture 22 simply rolled around itself within suture cassette 24. FIG. 1B shows a spool 30 and spool wheel 32. Here suture 22 is wound on spool 30 within suture cassette 24 by spool wheel 32. FIG. 1C shows suture 22 overlapped upon itself within suture cassette 24.

Referring now to FIGS. 2A-D, FIG. 2A shows a "Prior Art" drill shaft in which the drill shaft is of a uniform diameter from the first end to the second, as is known. This form is known and the Applicants have found it not to be preferred. Nonetheless, even this form of drill shaft when coupled with the other elements of Applicants' invention, are deemed useful, new and non-obvious improvements over the art.

Figure 2A:
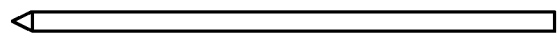
FIG. 2A is a side view of a Prior Art drill shaft.
Figure 2B:
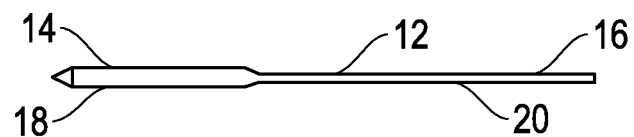
FIG. 2B is a side view of the drill shaft of the present invention with a first diameter that is larger than a second diameter.
Figure 2C:
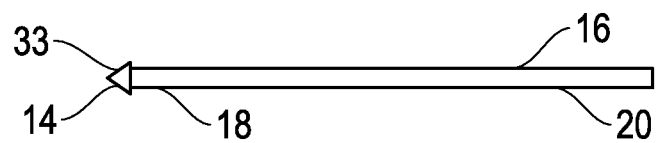
FIG. 2C is the invention of FIG. 2B where the first diameter is in the form of an "acorn" shaped drill head.
Figure 2D:
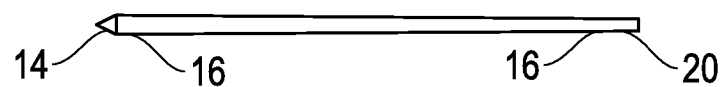
FIG. 2D is the invention of FIG. 2B where the first diameter begins at the first end of the drill shaft and tapers along its length to the second end of the drill shaft.

Importantly, again, however, the preferred embodiment of the present invention includes a drill shaft 12 with a first diameter 14 and a second diameter 16 where the first diameter 14 is larger than the second diameter 16. This limitation is illustrated in FIG. 2B where first diameter 14 at first end 18 of drill shaft 12 is clearly larger than, and "steps down" to, the second diameter 16 of drill shaft 12 at the second end 20. The illustrations make clear that the diameters vary a lot or a little and cover a small part or more of the entire drill shaft 12. Thus, FIG. 2C shows drill shaft 12 with and "acorn" shaped drill head 33 at the very front of first end 18. Drill head 33 forms the first diameter 14 of drill shaft 12 and the second, smaller, diameter 16 forms the rest of drill shaft 12. Any formulation of large and small diameters may be seen as shown by the present invention and disclosure as at FIG. 2D where the drill shaft 12 starts with a large first diameter 14 at the first end 18 and then tapers in diameter in a regular manner all the way to the second end 20 of drill shaft 12. In any configuration, by this structure, in combination with the other elements of the invention as described herein, the prior art requirement of drilling two holes or a much larger hole so as to enable a suture to be passed, is eliminated and a single hole is made that accommodates a suture 22 by the drill shaft 12 in just one use, as will be described more fully hereafter.

Figure 3A:
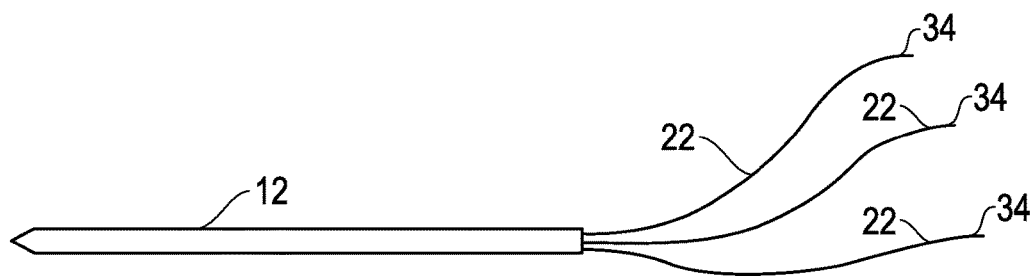
FIG. 3A shows multiple sutures attached to the drill shaft.
Figure 3B:
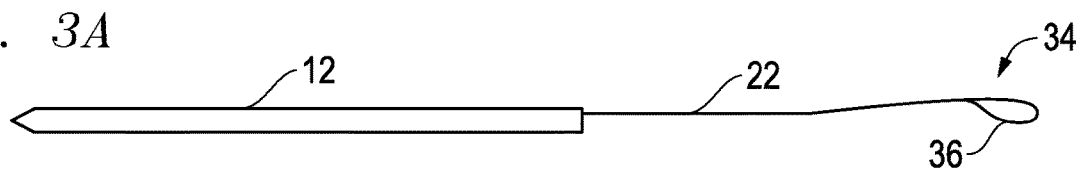
FIG. 3B shows a suture with a loop on the free end.
Figure 3C:
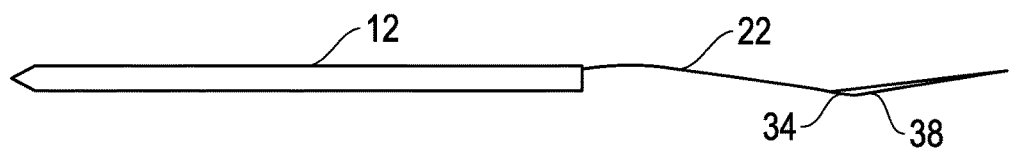
FIG. 3C shows a needle attached on the free end.
Figure 3D:
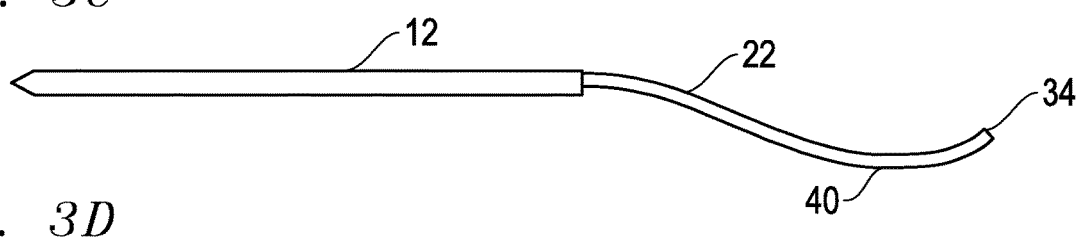
FIG. 3D shows the suture in the form of a tape.

Referring now to FIGS. 3A-D, other features of the invention are illustrated where, as at FIG. 3A, multiple sutures 22 are shown connected with drill shaft 12. FIG. 3B shows that the free end 34 of suture 22 includes a loop 36 which can be used for any useful purpose such as drawing another suture 22 through hole 50. FIG. 3C shows free end 34 connected with a needle 38. Certainly free end 34 may be connected to another section of suture 22 or any other useful thing as deemed necessary. FIG. 3D shows suture 22 in the form of a suture tape 40 as is known in the art and not described more fully hereafter. It should be understood by now that each of these examples illustrated in FIGS. 3A-D are compatible with being contained within suture cassette 24 (not shown) when used as shown by example only in FIGS. 1A-C.

Figure 4A:
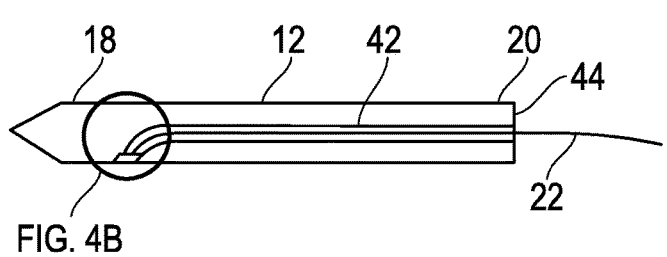
FIG. 4A is a side view of the drill shaft with one channel.
Figure 4C:
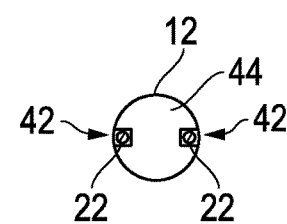
FIG. 4B is an enlarged view of FIG. 4A at the point where the channel exits the drill shaft near the first end of the drill shaft and FIG. 4C is an end view of FIG. 4A showing more than one channel in the drill shaft.
Figure 4B:
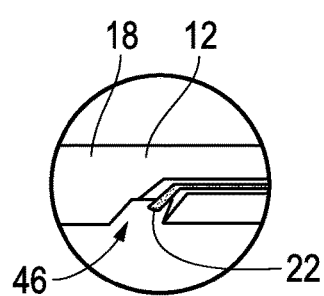

Referring now to FIGS. 4A-C, in one embodiment, drill shaft 12 includes at least one channel 42 in the drill shaft 12 where the at least one channel 42 starts at the second end 20 in the base 44 of the drill shaft 12 as shown and extends along the length of the drill shaft 12. The channel 42 includes an opening 46 in the drill shaft 12 at the first end 18. The at least one channel 42 is conformed to receive suture 22 and allows suture 22 to be introduced though drill shaft 12 as may be deemed useful. FIG. 4C shows two channels 42 and certainly more channels 42 are included within the invention.

Figure 5A:
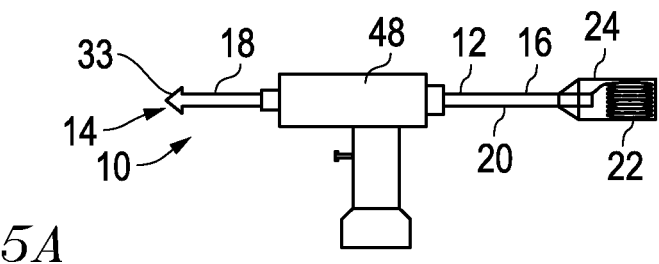
FIG. 5A shows the drill shaft connected with a drill, the drill shaft including a suture cassette with suture inside.
Figure 5B:
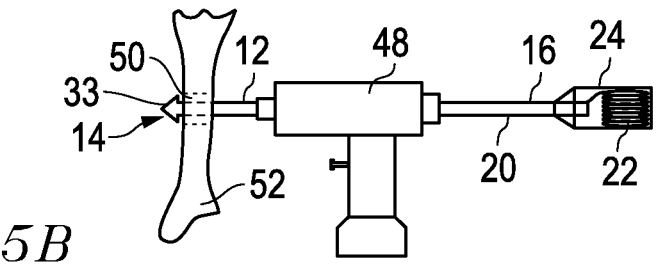
FIG. 5B shows the drill using the drill shaft to drill a hole through a bone.
Figure 5C:
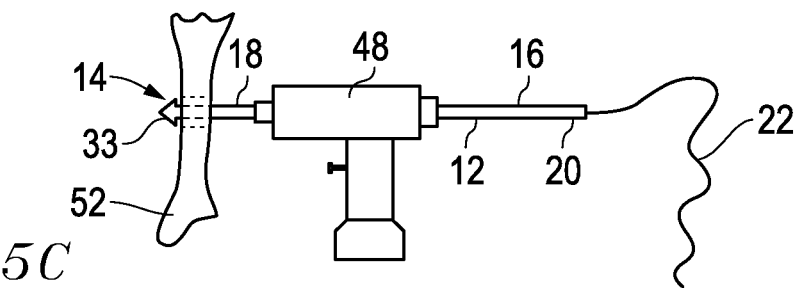
FIG. 5C shows the suture cassette removed and one end of the suture attached to the drill shaft and the other end of the suture free.
Figure 5D:
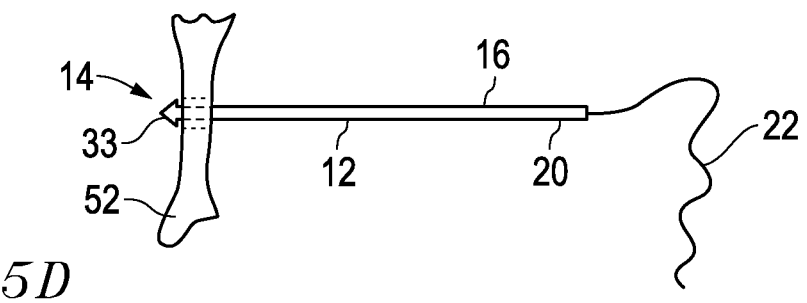
FIG. 5D shows the drill removed from the drill shaft.
Figure 5E:
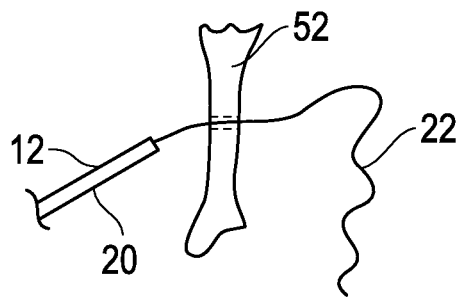
FIGS. 5 A-E illustrate the steps in the method of using the invention of FIG. 1 where.

Referring to FIGS. 5A-E the use and method of the present invention is illustrated. To begin with, it should be understood that drill shaft 12 starts the process as a separate element. That is, drill shaft 12, and suture cassette 24 when present, are assembled independently from drill 48. Then drill shaft 12 is introduced into cannulated (that is there is a hole through the drill 48 from front to back conformed to receive and releasably retain drill shaft 12) drill 48 and secured with drill 48 as is known such that operation of drill 48 rotates drill shaft 12. Thus, at FIG. 5A drill 48 is shown connected with drill shaft 12 with the first end 18 extending from the drill 48 on one side of the drill 48 and the second end 20 of the drill shaft 12 (shown with suture cassette 24) on the other side of drill 48. Once in place, drill 48 is operated in a customary manner to rotate drill shaft 12, with drill head 33, for example only. FIG. 5B shows the drill shaft 12 having drilled a hole 50 in bone 52, for example only. FIG. 5C shows suture cassette 24 removed and suture 22 freed. FIG. 5D shows drill 48 removed and FIG. 5D shows drill shaft 12 pulled completely through hole 50 in bone 52 along with some of suture 22 attached to drill shaft 12 such that some of the suture 22 is on one side of hole 50 and some of the suture 22 is on the other side of hole 50 as desired.

By way of continued explanation, the subject of this invention is a drill shaft 12 (to mean a wire, pin, or drill) with a suture 22 attached to the back end of the drill shaft 12 The suture 22 is preferably contained in a simple suture management system (i.e. suture cassette 24) which allows for drilling through bone 52 without damaging tangling and unraveling of the suture 22 during the drilling process as illustrated in FIGS. 5A-E. After the hole 50 is drilled, the suture cassette 24 is disengaged from the end of the drill shaft 12, unfurling the suture 22, the drill 48 removed, and allowing the drill shaft 12 to be pulled completely through the drill hole 50, pulling the suture 22 into the bone tunnel 50 in preparation to complete the repair procedure. This creates a "One-Pass" device for passing suture through bone.

To ensure smooth and easy passing of the drill shaft 12 through the hole 50, the drill shaft 12 should have a slightly larger distal (cutting) tip (first diameter 14 and acorn drill head 33) than the rest of the drill shaft 12 with a second smaller diameter 16. This creates a bone tunnel 50 that is slightly larger in diameter than the rest of the drill shaft 12, making it easy to pull the drill shaft 12 completely through the drill hole 50.

Applicants' one-pass suture drill device 10 has significant advantages over prior methods used for the purpose of passing suture through boney tunnels, which can then be used to attach soft tissue to bone. Unlike current devices, this one-pass device both drills the tunnel and passes the suture through that same tunnel, negating the need for drill bits, separate suture passer loops or other passing devices, and creates an easy way to avoid soft tissue entanglement and inability to find the bone tunnel when trying to pass suture through bone with traditional devices. This decreases the surgical time required, limits soft tissue dissection, and reduces frustration to the surgeon. This is especially true around the patella tendon or quadriceps tendon but can also be used about the distal fibula, tarsal navicular, greater trochanter of the femur, and proximal humerus as well as other locations in the skeleton.

Still further, sutures passed through bone tunnels can be advantageous in comparison to use of bone anchors. For example, when the patella tendon is repaired to the patella in a patient that later undergoes total knee arthropasty with patellar resurfacing, the presence of suture anchors placed in the patella for the original repair will significantly interfere with patella resurfacing. The same issues present when around the ankle after ligament repair. If conversion to an ankle fusion or arthroplasty is required at a later date, suture anchor implants in bone could affect the ability to place proper implants and could create significant metallosis when drilling through these areas. The one-pass device of the present invention 10 simply and solely deploys suture through tight bone tunnels for the purpose of soft tissue reattachment, and leaves no extraneous metal in the skeleton. Conceivably this would also reduce the risk of infection as well, in that no foreign metal body would be left behind.

Again, the completed device of the present invention 10 could take a couple different forms. This could be a straight drill with slightly enlarged head (i.e. acorn tip) and the suture swedged on the drill shaft at the back end of the drill shaft or it could be a tapered drill shaft with reduced diameter toward the back. In addition the suture management cassette 24 could be secured onto the back end of the drill shaft 12 as shown and described above.

Sutures 22 could be single or multiple, made of woven thread suture material, flexible wire or other implantable materials such as gortex or tapes that are required to pass through bone tunnels. The suture could be free at the back end, or swedged to a straight needle, or looped. Looping the end may allow capture of another suture or device to be brought through bone using the suture drill apparatus 10 of the present invention.

The suture holding cassette 24 holds securely to the drill shaft and therefore spins with the drill shaft 12, thus keeping the suture 22 from unraveling or tangling or flopping around the sterile field or creating other possible irregularities or damage to the suture. The cassette makes suture management predictable and controllable while drilling through soft tissue and bone, and prevents suture 22 from spinning outside the sterile field. Inside the cassette 24, the suture 22 could lay folded and packed within the cassette or wound onto a spool 30 within the cassette that could have an external thumb screw/spool wheel 32 to tighten tension on suture within the module or other forms to achieve management/control of the suture while drilling.

The cassette 24 is able to be easily removed from the end of the drill shaft, then the suture 22 unfurled, allowing it to be pulled into the bone tunnel as the drill shaft is pulled all the way through the newly created bone tunnel (hole 50). In addition, the suture cassette can be designed to reload remaining amounts of suture and re-secured back onto the drill shaft after the first pass through bone for additional uses as for example by means of an external thumb screw/spool wheel 32 or at least one channel 42 as described with regard to FIGS. 4A-C.

The invention of the present device is intended for both human and veterinary applications as described above, however the technology could also be applied in the drilling of soft structures through materials in the construction trades such as rope or wire through wood or metal.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:
1. A suture drill apparatus comprising:
   a. a drill shaft with a first end and a second end and a cannulated drill wherein said drill shaft is conformed to connect with the cannulated drill such that the cannulated drill is located between the first end of the drill shaft and the second end of the drill shaft;

b. a suture connected with said drill shaft and a suture cassette wherein said suture is enclosed within said suture cassette; and c. an attachment device connecting said suture cassette to said drill shaft such that said suture cassette rotates with said drill shaft and such that said suture and said suture cassette do not move relative to the drill shaft when connected with said drill shaft wherein said attachment device is removably connectable with said drill shaft.

2. The apparatus of claim 1 wherein said first end includes a drill head wherein said drill head forms a larger first diameter of said drill shaft.

3. The apparatus of claim 1 further including more than one suture connected with said drill shaft.

4. The apparatus of claim 1 wherein the attachment device is one selected from a group consisting of: a press fit connection, a pin and a spring and notch combination.

5. The apparatus of claim 1 wherein said first end includes a larger first diameter section and said second end includes a smaller second diameter section.

6. The apparatus of claim 5 wherein said larger first diameter tapers along the drill shaft from said first end to a smaller second diameter at said second end.

7. The apparatus of claim 1 wherein said suture includes a first end and a second end and said first end of said suture is connected with said drill shaft and said second end of said suture includes a loop.

8. The apparatus of claim 7 wherein said second end of said suture is connected with a needle.

9. A suture drill apparatus comprising:
a. a drill shaft with a first end and a second end and a cannulated drill wherein said drill shaft is conformed to connect with the cannulated drill, the cannulated drill having a front and a back such that the cannulated drill is located between the first end of the drill shaft and the second end of the drill shaft and such that the first end of the drill shaft extends beyond the front of the cannulated drill and the second end of the drill shaft extends beyond the back of the cannulated drill;

b. a suture connected with said drill shaft such that said suture extends from said second end of said drill shaft and such that upon removal of said drill shaft from said front of said cannulated drill, said suture passes through said cannulated drill from said back and out of said front of said cannulated drill; and c. a suture cassette wherein said suture is enclosed within said suture cassette wherein said suture cassette includes an attachment device connecting said suture cassette to said drill shaft such that said suture cassette is removably connectable with said drill shaft at said second end of said drill shaft and such that said suture cassette rotates with said drill shaft and such that said suture and said suture cassette do not move relative to the drill shaft when connected with said drill shaft and such that said suture cassette is completely removable from said second end of said drill shaft when said suture cassette is disconnected from said drill shaft.

10. The apparatus of claim 9 wherein said drill shaft is selected from a group consisting of: a drill shaft with an acorn tip; a drill shaft with a stepped diameter and a drill shaft that is tapered from the first end to the second end.

11. The apparatus of claim 9 wherein said suture is selected from a group of sutures consisting of: thread, flexible wire and implantable tape.

12. The apparatus of claim 9 wherein said drill shaft includes at least one channel in said drill shaft, said at least one channel starting at said second end and extending along the length of said drill shaft with an opening in a side of said drill shaft at said first end, said at least one channel conformed to receive said suture.

13. The apparatus of claim 9 further including more than one suture connected with said drill shaft.

14. The apparatus of claim 9 wherein said cannulated drill is a cannulated power drill.

15. The apparatus of claim 9 wherein the attachment device is one selected from a group consisting of: a press fit connection, a pin and a spring and notch combination.

16. The apparatus of claim 9 wherein said suture includes a first end and a second end and said first end of said suture is connected with said drill shaft and said second end of said suture includes a loop.

17. The apparatus of claim 16 wherein said second end of said suture is connected with a needle.

18. A suture drill method comprising the steps of:
a. providing a drill shaft with a first end and a second end; a cannulated drill
wherein said drill shaft is inserted into and connected with the cannulated drill, the cannulated drill having a front and a back such that the cannulated drill is located between the first end of the drill shaft and the second end of the drill shaft and such that the first end of the drill shaft extends beyond the front of the cannulated drill and the second end of the drill shaft extends beyond the back of the cannulated drill; a suture connected with said drill shaft such that said suture extends from said second end of said drill shaft; and a suture cassette wherein said suture is enclosed within said suture cassette wherein said suture cassette includes an attachment device connecting said suture cassette to said drill shaft such that said suture cassette is removably connectable with said drill shaft at said second end of said drill shaft and such that said suture cassette rotates with said drill shaft and such that said suture and said suture cassette do not move relative to the drill shaft when connected with said drill shaft and such that said suture cassette is completely removable from said second end of said drill shaft when said suture cassette is disconnected from said drill shaft;

b. drilling a hole with said drill shaft;

c. disconnecting said suture cassette from said drill shaft and removing said suture cassette;

d. removing said cannulated drill from the second end of said drill shaft such that said suture passes through said cumulated drill from said back and out of said front of said cannulated drill; and e. pulling said drill shaft and said suture through said hole.

19. The method of claim 18 wherein said drill shaft is selected from a group consisting of: a drill shaft with an acorn tip; a drill shaft with a stepped diameter and a drill shaft that is tapered from the first end to the second end.

20. The method of claim 18 wherein the attachment device is one selected from a group consisting of: a press fit connection, a pin and a spring and notch combination.

* * * * *